United States Patent [19]

Franken et al.

[11] Patent Number: 5,342,352
[45] Date of Patent: * Aug. 30, 1994

[54] LASER DEBRIDEMENT OF WOUNDS

[76] Inventors: Peter A. Franken, 2105 E. 4th St., Tuscon, Ariz. 85721; Alan E. Hill, 17 Elarco Rd., Albuquerque, N. Mex. 87123

[*] Notice: The portion of the term of this patent subsequent to May 4, 2010 has been disclaimed.

[21] Appl. No.: 43,274

[22] Filed: Apr. 6, 1993

Related U.S. Application Data

[63] Continuation-in-part of Ser. No. 679,421, Apr. 2, 1991, abandoned.

[51] Int. Cl.⁵ ............................................. A61B 5/00
[52] U.S. Cl. ..................................... 606/9; 128/669; 606/19; 606/3
[58] Field of Search ................... 606/2, 3, 9, 11, 12, 606/13, 17, 18, 19; 128/664, 669

[56]          References Cited
U.S. PATENT DOCUMENTS

| | | | |
|---|---|---|---|
| 3,913,582 | 10/1975 | Sharon | 606/19 |
| 4,917,083 | 4/1990 | Harrington et al. | 606/19 |
| 4,917,084 | 4/1990 | Sinofsky | 606/3 X |
| 5,074,306 | 12/1991 | Green et al. | 128/664 |
| 5,207,671 | 5/1993 | Franken | 606/9 |

OTHER PUBLICATIONS

Use Of A Carbon Dioxide Laser For The Debridement Of Third Degree Burns: Levine et al., Annals of Surgery, vol. 179, No. 2, pp. 246–252, Feb. 1974.
Laser Excision of Acute Third Degree Burns Followed By Immediate Autograft Replacement: An Experimental Study In The Pig, Stellar et al., Journal of Trauma, vol. 13, No. 1, pp. 45—53, Jan., 1973.

*Primary Examiner*—Peter A. Aschenbrenner
*Attorney, Agent, or Firm*—Reising, Ethington, Barnard, Perry & Milton

[57]          ABSTRACT

A technique is disclosed for wound debridement in which a pulsed $CO_2$ laser beam is caused to impinge upon exposed tissue with individual pulses sufficiently energetic to ablate a thin layer of tissue. Each pulse has a time duration short enough to cause ablation but long enough so that it does not cause atmospheric breakdown. The $CO_2$ laser, with a wavelength in the far infrared region, is operated to produce a pulsed beam with individual pulses having an energy of about one joule per pulse or greater. The beam is focused to produce a beam diameter with a fluence of approximately ten joules per square centimeter at the tissue to be ablated and with a pulse repetition rate of approximately one hundred pulses per second and a pulse duration between one microsecond and ten microseconds. In operation, the ablation of eschar is achieved over a relatively wide range of angles of incidence without need for change of the beam parameters.

9 Claims, 1 Drawing Sheet

LASER DEBRIDEMENT OF WOUNDS

This is a continuation-in-part application of U.S. Ser. No. 07/679,421, filed Apr. 2, 1991 now U.S. Pat. No. 5,207,671.

FIELD OF THE INVENTION

This invention relates to the use of a laser as a medical instrument; more particularly, it relates to laser debridement of wounds.

BACKGROUND OF THE INVENTION

There has been a longstanding need for a new surgical technique for debridement of wounds, especially burn wounds, which will significantly lessen the trauma and enhance healing. Laser surgery has held the hope for fulfillment of the need but, for two decades, a successful laser technique has eluded the investigators.

Laser beams are used in a variety of surgical procedures. Earlier investigators have undertaken to utilize the laser for ablation of tissue in treating surface lesions of the skin and dermatologists are using such devices today. However, there has been negligible success in treating burn wounds. While there are certain inherent advantages afforded by laser surgery for serious burns, these cannot be availed of unless the time required for the surgical procedure becomes at least comparable to that in the conventional scalpel surgery presently used in serious burn cases and unless the debridement leaves a tissue bed that will take a viable skin graft.

A serious burn on the human body usually extends well below the superficial skin surface. A significant thickness of tissue dies as a result of the thermal assault and this necrotic material develops into a scar mass called eschar. The interface between the eschar and the sublying viable tissue is a fertile anaerobic region for growth and propagation of infection. The current technique for medical treatment involves debridement (i.e., removal) of the eschar by a surgical procedure called "tangential excision", accomplished with a scalpel. After the debridement, the exposed viable tissue is covered with a skin graft which provides protection against fluid loss and contamination and initiates the healing process. This surgical procedure is known to be highly traumatic. Debridement by tangential excision for severe and extensive burn wounds may require many hours for the procedure and there is an attendant very high loss of blood during the debridement. Much effort has been expended by investigators in seeking to develop a laser debridement technique to replace the scalpel excision technique with its attendant trauma.

The Prior Art

Levine et al have reported the investigation of the use of a carbon dioxide ($CO_2$) laser for the excision of third degree burns with a view toward minimizing blood loss and minimizing damage to the underlying tissue. See "Use Of A Carbon Dioxide Laser For The Debridement Of Third Degree Burns", Levine et al, *Annals of Surgery*, Volume 179, No. 2, pages 246 through 252, February, 1974. This report describes an instrument comprising a $CO_2$ laser with an articulated surgical arm which permits the laser beam to be focused by a system of mirrors and an output lens in the handpiece held by the operating surgeon. The $CO_2$ laser is described as having a power output which is variable from zero to forty watts with a beam having a wavelength in the far infrared region at 10.6 microns. It is reported that the laser was operated with a continuous wave output which enables use of the laser as a scalpel in general surgical procedures. The report describes an initial technique of "laser vaporization" in which the beam was directly focused on the burned tissue. It was reported that this method was found to be too slow and that injury to underlying tissue often occurred. It also describes use of the laser as a scalpel, a technique referred to as "laser excision". In this, the laser is first used to incise a rim of tissue completely surrounding the burned area; then a flap of tissue containing the burned skin was dissected free of the underlying tissue, using the laser as a "photo knife" or scalpel. Laser debridement of burns using the same type of $CO_2$ laser and similar procedure is described in "Laser Excision of Acute Third Degree Burns Followed By Immediate Autograft Replacement: An Experimental Study In The Pig" by Stellar et al, *Journal of Trauma*, Volume 13, No. 1, pages 45 through 53, January, 1973. In the described procedure with the $CO_2$ laser operated in the continuous wave mode, the removal of tissue is described as "laser vaporization" in which the laser is directly focused on the burned tissue, converting it to smoke.

Also, in the prior art, it is known to use the ablative effects of a laser beam in a dermatological procedure for removing thin lesions, such as port wine scars and warts. In this technique, a $CO_2$ laser is operated in a pulsed mode with the beam applied perpendicularly to the burned surface. This dermatological laser is operated with pulses of less than 0.1 microseconds duration at a repetition rate of about one pulse per second with two or three joules per pulse. This dermatological laser is infeasible for removing eschar over large areas because it is too slow; it would, for example, take many hours to ablate the eschar from an entire limb.

Carbon dioxide lasers are currently available which, typically, emit pulses of infrared radiation at 10.6 microns wavelength in the regime of several joules per pulse. These lasers have a characteristically short pulse length, less than 0.1 microsecond, as an inherent feature of their design. Such lasers are used for various purposes in the manufacturing industry and are also used as surgical cutting instruments. Such lasers are of the so-called TEA type and are available from Lumonics Company and Coherent Radiation, Inc., for example.

Events Leading To The Invention Disclosed In This Patent

We made the invention set forth below in the course of our undertaking to provide an improved technique for the debridement of burns which will greatly reduce the time required for the procedure, impose significantly less traumatic effect and enhance skin graft and healing of the wound. It was our objective to utilize a laser to ablate the eschar of a burn wound in such a manner that a high rate of removal would be realized without significant injury to the viable tissue.

The above-mentioned dermatological $CO_2$ laser is not capable of achieving our objective because of the very low rate of ablation which can be realized. The use of a $CO_2$ laser of the TEA type was researched with the objective of achieving a high rate of ablation by using a high pulse repetition rate, say 100 pulses per second. The TEA laser delivers an output energy of about three joules per pulse in a beam approximately one centimeter in diameter. The fluence of deposited energy with this beam, about four joules per square centimeter, is not enough to ablate the surface layer of eschar. However, with an infrared transmitting lens, the diameter of the beam impinging on the surface can be reduced sufficiently so that the fluence, i.e. the joules per square centimeter, is high enough to ablate the surface layer. It was found that the required fluence could not be achieved with the laser without causing atmospheric breakdown which was found to occur at a fluence of about ten joules per square centimeter. The atmospheric breakdown and attendant electric discharge commences within a small fraction of a microsecond after laser pulse initiation and the resulting plasma shields the eschar from absorbing the remaining energy from the laser pulse. Thus, the commercial TEA type of $CO_2$ laser was found to be incapable of achieving our objective.

This led our investigation to the discovery that successful ablation can be realized with a pulsed beam of correlated pulse duration and energy fluence. With such correlation, a high pulse repetition rate can be used. Further, it was realized that the laser beam energy is absorbed by only a few wavelengths penetration of water-laden tissue and thus, the surgeon could control the beam manually to ablate the eschar without significant injury to the viable tissue.

SUMMARY OF THE INVENTION

We have discovered that the objectives of our invention are achieved by a wound debridement technique in which a pulsed laser beam is caused to impinge upon a layer of exposed tissue with individual pulses sufficiently energetic to ablate the thin layer of tissue, each pulse having a time duration short enough to cause the ablation but long enough so that it does not cause atmospheric breakdown.

Further, in accordance with this invention, the pulsed laser beam is produced by a $CO_2$ laser having a wavelength in the far infrared region. Further, with a $CO_2$ laser, the individual pulses have an energy of preferably about one joule per pulse or greater. Further, the laser beam is produced with pulses having a duration between one microsecond and ten microseconds. Further, the laser beam has a diameter at the tissue so that a fluence of approximately ten joules per square centimeter is realized. Further, the laser beam has a pulse repetition rate in the range of approximately fifty to one hundred fifty pulses per second.

A complete understanding of this invention may be obtained from the detailed description that follows.

BEST MODE FOR CARRYING OUT THE INVENTION

Figure 1:
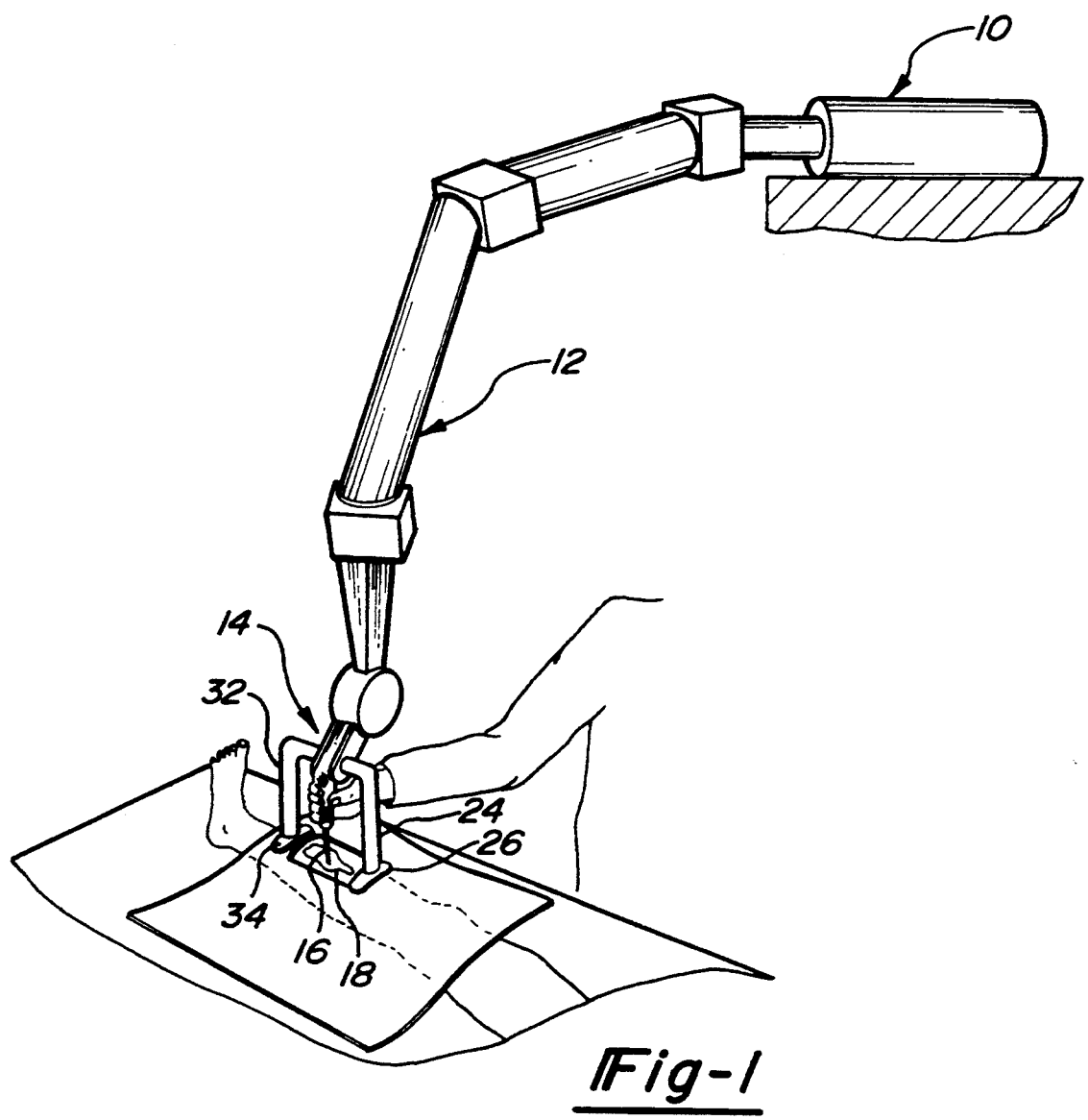
FIG. 1 is a perspective view of apparatus for carrying out the invention.

An illustrative embodiment of the invention will now be described utilizing a pulsed $CO_2$ laser for debridement by ablation of the eschar of a burn wound. It will be appreciated, as the description proceeds, that the invention may be realized in other embodiments and may be utilized in various applications.

Referring now to the drawing, apparatus is illustrated for carrying out the invention. The apparatus comprises a $CO_2$ laser 10 and an optical delivery system 12 in the form of an articulated surgical arm. The delivery system 12 has its input coupled with the output of the laser 10 and includes a beam output head 14 which is adapted to be hand-held and manually manipulated with complete freedom of movement, both angularly and translationally. The laser beam 16 is emitted from the end of the head 14 and by manipulation thereof, the beam may be directed as desired. As illustrated, the beam 16 is caused to impinge approximately perpendicularly on the surface of the eschar 18 of a burn wound. The head 14 (or a foot pedal) is provided with a control switch, not shown, for turning the beam 16 on and off. The surgical apparatus may also include lighting on the head 14, and a means for controlling the pulse repetition rate. Preferably, the apparatus is provided with means for clearing, from the path of the laser beam, smoke or other debris resulting from the ablation of eschar or the tissue. It is also desirable to blow away any collected blood or other fluid in the area of impingement of the laser beam. For this purpose, the beam output head 14 is fitted with an air conduit 24 which is provided with an output nozzle 26 adjacent the laser beam and directed across the surface of the wound. An air blower, not shown, is connected with conduit 24. The nozzle is adapted to provide a thin, laminar stream of air flow over the surface of the wound at the area of beam impingement with a sufficiently high velocity to clear the air and wound surface between laser pulses. For a pulse rate of about one hundred pulses per second an air flow at the speed of about mach 0.1 or 0.2 is desirable. In order to collect the smoke and debris entrained in the air flow over the wound, a vacuum cleaner, not shown, is connected with a conduit 32 extending to an intake opening 34 opposite the nozzle 26. Thus, the beam path is cleared of smoke and other debris which would otherwise adversely affect the transfer of energy from the laser beam to the wound.

The $CO_2$ laser 10 emits pulses of infrared radiation at 10.6 microns wavelength. The laser is capable of delivering individual pulses which may be selectively preset to comprise energy in the range of several joules per pulse. The laser may also be preset to produce pulses having a duration between one and ten microseconds and to produce a pulse repetition rate in the range of approximately fifty to one hundred fifty pulses per second. The optical delivery system is provided with optical focusing to vary the beam diameter at the surface of the tissue so that a fluence of approximately ten joules per centimeter can be realized. The infrared energy is uniformly distributed over the cross-section of the beam within about ten percent variation. A laser with these capabilities is available from Plasmatronics of Albuquerque, N.M.

In accordance with the invention, the method of wound debridement is as follows. The $CO_2$ laser 10 is operated to produce a pulsed beam with individual pulses having an energy of about one joule per pulse or greater. The beam is focused to produce a beam diameter at the tissue so that a fluence of approximately ten joules per square centimeter is realized. If the energy per pulse is increased, the beam size may be increased to cover a larger area of tissue with the fluence being maintained at approximately ten joules per centimeter. The laser is operated with a pulse repetition rate in the range of approximately fifty to one hundred fifty pulses per second with a pulse duration between one microsecond and ten microseconds. If the pulse duration is much less than one microsecond, atmospheric breakdown may occur and preclude ablation of tissue. If the pulse duration is increased significantly beyond ten microseconds, the result will be a very deleterious smoking and cauterization, accompanied by heat penetration into the sublying living tissue.

With the laser operating as set forth above, the surgeon manipulates the beam head 14 to cause the beam to impinge on selected eschar to ablate the eschar over the required area. Experiments using this method demonstrate that eschar may be removed at a high rate without atmospheric breakdown. Experiments were conducted on a fully anesthetized fifty pound piglet. Four burns, each of one square inch, treated with this method permitted remarkably successfully skin grafts. The surgeon was able to learn the technique in a matter of minutes even though the experimental optical delivery system was rather crude. It was found that the surgeon had no difficulty in controlling the beam in order to achieve satisfactory ablation without significant damage to underlying viable tissue. It is believed that the experimental work shows that the damaged layer is thin enough so that the attendant subfusing of liquids is sufficient to adequately "wash" the bed and thus increase the viability of the subsequent skin graft. The damage level is believed to be less than a few microns, an amount which has no clinical significance to subsequent skin grafting.

In operation of the laser as described above, the beam is manipulated to ablate successive regions of eschar. A high rate of ablation, as discussed above, is achieved when the beam impinges on a layer of eschar at angles within a wide range of angularity from a direction perpendicular to the eschar layer. The ablation rate is substantially independent of the angle of incidence within a given range. The reason for this is set forth below.

Figure 2:
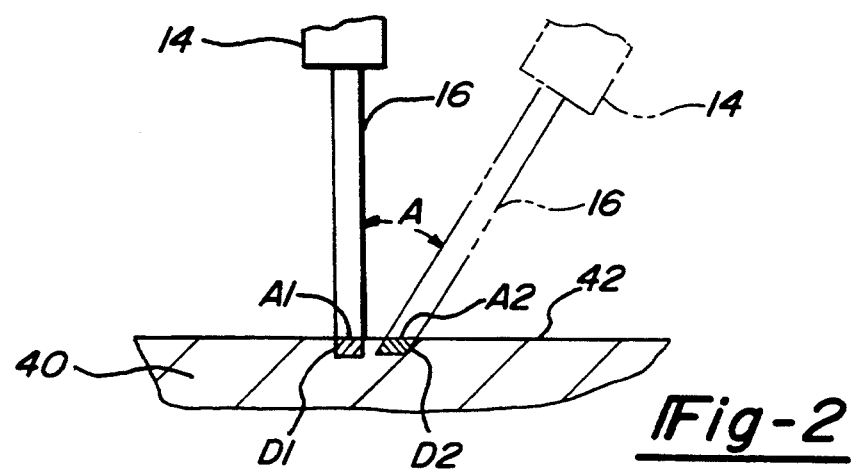
FIG. 2 depicts a laser beam with different angles of incidence on a surface.

The effect of changing the angle of incidence of the laser beam is illustrated in FIG. 2. In this figure, the laser beam 16 emitted from the head 14 in one position (shown in uninterrupted lines) impinges upon the surface 42 of a body 40. The beam 16 is perpendicular to the surface 42 and has an angle of incidence equal to zero. With the laser head 14 in an alternate position (shown in interrupted lines), the laser beam 16 impinges upon the surface 42 with an arbitrary angle of incidence equal to A. The fluence of the beam in the area of impingement on the surface 42 will decrease proportional to cosine A. This is because the area impacted by the beam will increase as 1/cosine A. This is the obliquity effect. On the other hand, the depth to which the radiation will go (before intensity is reduced by about one-half) will decrease according to cosine A just because of penetration effects. The obliquity effect is illustrated by the difference of the impact areas shown in FIG. 2 as A1 and A2 and the difference in depth of penetration is indicated by the dimensions D1 and D2. Accordingly, the deposition of radiant energy per unit volume in the upper layer of tissue will be independent, to first order, of departures from perpendicularity over a wide range of angles. As the angle of incidence A is increased to values of about twenty degrees or more the energy per unit volume in the upper layer of eschar, and hence the ablation rate, may begin to decrease. At angles of incidence greater than about thirty degrees, there is a diminution of the radiant energy per unit volume which may cause a decrease of ablation rate by a few percent, say about ten percent or less, of that which is achieved with an angle of incidence equal to zero degrees.

The surface of the eschar has a topography which is characterized by somewhat irregular contours due to anatomy as well as pits and ridges in the eschar itself. The resultant angular variations relative to a beam directed perpendicular to the surface are typically less than about thirty degrees. Accordingly, with the laser beam impinging upon a layer of eschar at angles ranging from about zero degrees to about thirty degrees from a direction perpendicular to the eschar layer, high rates of ablation are achieved. If the angle of incidence is increased much beyond thirty degrees, there may be some degradation of the ablation rate. This can be compensated for by changing the beam parameters to increase the fluence of the beam. For this, the beam may be focused to a smaller diameter or the energy per pulse may be increased or a combination of both.

In some cases, depending upon the topography of the eschar, the rate of ablation may diminish undesirably upon movement of the beam from one region of eschar to another. This might arise, for example, where the beam is moved from a relatively smooth region to a region having a very rough surface, i.e. deep pits and high ridges. This may result in impact of the beam over an actual area considerably greater than the cross-sectional area of the beam so that there is a significant decrease in the effective fluence of the beam. In this case, the rate of ablation may be restored by increasing the fluence of the beam. This can be accomplished by optically focusing the beam to decrease the beam diameter. Also, it may be accomplished by increasing the energy per pulse or by a combined adjustment of the beam diameter and energy per pulse.

In some situations, the topography may include a vertical ridge of eschar or other unwanted tissue. In this case, the ridge may be most efficiently removed by tilting the beam sufficiently to impact the ridge near its base to excise it from the sub-lying tissue. For this purpose, it may be desirable to line-focus the beam, i.e. decrease the beam diameter to a narrow line and concomitantly, if necessary, reduce the energy per pulse so that a fluence of about ten joules per centimeter is maintained.

As mentioned above, it is desirable to remove the smoke and other debris which results from ablation. Such debris tends to form a cloud over the ablated area. By directing the laser beam at a large angle of incidence, the beam path can be more effectively cleared of debris and the splatter onto the laser and the beam transmission optics is reduced.

As used herein, the term "ablate" is used to mean the blowing off of tissues by the absorption of pulses of intense radiation such as that produced by a laser. In the ablation process with short pulsed lasers a large quantity of heat energy is absorbed almost instantaneously in a very thin layer of the eschar which literally explodes. It is believed that part of this is due to actual evaporation of surface tissue and part of it arises from an enormous internal pressure developed by the vaporization of water in the tissue which, in turn, literally explodes the material away from the surface. The term "instantaneous" as just used means time periods of one microsecond or so which are extremely short compared to the time it takes for heat to diffuse into sublying tissue to the point where significant damage could be caused.

Further, as used herein, the term "atmospheric breakdown" is used to mean a phenomenon which occurs when the electric field component of a beam of radiant energy becomes strong enough to cause actual electrical discharge characterized by a flash of visible light and accompanied by a "cap pistol sound". Atmospheric breakdown occurs when the intensity of a 10.6 micron wavelength beam exceeds 20 to 50 megawatts per square centimeter, depending on the cleanliness of the air in the path of the beam.

Although the description of this invention has been given with reference to a particular embodiment, it is not to be construed in a limiting sense. Many variations and modifications will now occur to those skilled in the art. For a definition of the invention reference is made to the appended claims.

What is claimed is:

1. The method of debridement of eschar from a burn wound comprising the steps of:
   producing a pulsed laser beam with individual pulses sufficiently energetic to ablate a layer of eschar, said laser beam having an average power of at least one hundred joules per second, each pulse having a time duration short enough to avoid deleterious heat penetration and long enough so that it does not cause breakdown of the atmosphere,
   and causing said beam to impinge upon said layer of eschar at an angle of incidence ranging from zero degrees to about thirty degrees, said angle of incidence being measured from a direction perpendicular to said eschar layer.

2. The invention as defined in claim 1 including the steps of:
   increasing the fluence of the beam to increase the rate of ablation if the rate of ablation diminishes upon movement of the beam from one region of eschar to another because of a change of the topography of the eschar.

3. The invention as defined in claim 2 wherein said step of increasing the fluence includes:
   decreasing the beam diameter.

4. The invention as defined in claim 2 wherein the step of increasing the fluence includes:
   increasing the energy per pulse.

5. The invention as defined in claim 1 wherein said step of producing a pulsed laser beam includes:
   producing said laser beam with a $CO_2$ laser having a wavelength in the far infrared region at 10.6 microns.

6. The invention as defined in claim 5 wherein said step of producing a pulsed laser beam includes:
   producing said laser beam with individual pulses having an energy of about one joule per pulse or greater.

7. The invention as defined in claim 5 wherein said step of producing a pulsed laser beam includes:
   producing said laser beam with pulses having a duration between one microsecond and ten microseconds.

8. The invention as defined in claim 5 wherein said step of producing a pulsed laser beam includes:
   producing said laser beam with a beam cross-section at said eschar so that a fluence of approximately ten joules per square centimeter is realized.

9. The invention as defined in claim 5 wherein said step of producing a pulsed laser beam includes:
   producing said laser beam with the pulse repetition rate in the range of fifty to one hundred fifty pulses per second.

* * * * *